United States Patent
Pommerville

(12) 
(10) Patent No.: US 6,667,296 B1
(45) Date of Patent: Dec. 23, 2003

(54) METHOD FOR PREVENTING AND REDUCING RADIATION CYSTITIS USING HYALURONIC ACID

(76) Inventor: Peter J. Pommerville, 614 Inglewood Terrace, Victoria, British Columbia (CA)

( * ) Notice: Subject to any disclaimer, the term of this patent is extended or adjusted under 35 U.S.C. 154(b) by 0 days.

(21) Appl. No.: 09/830,063

(22) PCT Filed: Oct. 22, 1999

(86) PCT No.: PCT/CA99/00994

§ 371 (c)(1),
(2), (4) Date: Jul. 30, 2001

(87) PCT Pub. No.: WO00/24387

PCT Pub. Date: May 4, 2000

Related U.S. Application Data

(60) Provisional application No. 60/105,184, filed on Oct. 22, 1998.

(51) Int. Cl.[7] .................. A61K 31/715; C08B 37/00
(52) U.S. Cl. .................. 514/54; 536/53; 536/123.1
(58) Field of Search .................. 514/54; 536/53, 536/123.1

(56) References Cited

U.S. PATENT DOCUMENTS

| | | |
|---|---|---|
| 5,880,108 A | 3/1999 | Morales et al. |
| 6,232,301 B1 * | 5/2001 | Takahashi et al. ............ 514/54 |

FOREIGN PATENT DOCUMENTS

| | | |
|---|---|---|
| CA | 2 247 389 | 7/1998 |
| WO | WO 96/25168 | 8/1996 |
| WO | WO 97/03699 | 2/1997 |

OTHER PUBLICATIONS

Downey, Joe et al., "Relative Efficacy of Various Exogenous Glycosaminoglycans in Providing a Bladder Surface Permeability Barrier", Journal of Urology, 1997, pp. 128, vol. 157, issue 4 Suppl.

Liguori, Vincenzo et al., "Double–Blind, Randomized Clinical Study Comparing Hyaluronic Acid Cream to Placebo in Patients Treated With Radiotherapy", Radiotherapy and Oncology, 1997, pp. 155–161, vol. 42, issue 2.

Nickel, J. Curtis et al., "The Bladder Mucus (Glycosaminoglycan) Layer in Interstitial Cystitis", The Journal of Urology, Apr. 1993, pp. 716–718, vol. 149.

Oken, Martin M. et al., "Toxicity and Response Criteria of the Eastern Cooperative Oncology Group", Am. J. Clin. Oncol., 1982, pp. 649–655, vol. 5.

O'Leary, Michael P. et al., "The Interstitial Cystitis Sympton Index", Proceedings of the American Urological Association, May 1996, pp. 439A, vol. 155 supplement.

Porru, Daniele et al, "Results of Treatment of Refractory Interstitial Cystitis with Intravesical Hyaluronic Acid", Urologia Internationalis, 1997, pp. 26–29, vol. 59, issue 1.

Strohmaier, W.L., "Therapie der Interstitiellen Bzw. Radiogenen Zystitis mit D Glukosamin", Helv. Chir. ACTA, 1989, pp. 323–325, vol. 56.

* cited by examiner

*Primary Examiner*—Kathleen K. Fonda
(74) *Attorney, Agent, or Firm*—Kilpatrick Stockton LLP

(57) ABSTRACT

A method for preventing, reducing or treating radiation cystitis caused by external beam radiation therapy, which impinges on the urinary bladder and associated structures, comprising administering into the urinary bladder and associated structures a composition comprising hyaluronic acid (HA) having an average molecular weight of not less than $2 \times 10^5$ Daltons and a pharmaceutically acceptable carrier.

28 Claims, No Drawings

METHOD FOR PREVENTING AND REDUCING RADIATION CYSTITIS USING HYALURONIC ACID

CROSS REFERENCE TO RELATED APPLICATIONS

This application is the U.S. National stage entry under 35 U.S.C. 371 of PCT/CA99/00994 filed Oct. 22, 1999 and claims U.S. Provisional Application Serial No. 60/105,184, filed Oct. 22, 1998.

TECHNICAL FIELD

The present invention relates to a method for preventing, reducing and treating radiation cystitis caused by external beam radiation therapy, which impinges on the urinary bladder and associated structures, comprising administering into the urinary bladder and associated structures a composition comprising hyaluronic acid (HA) having an average molecular weight of not less than $2 \times 10^5$ Daltons and a pharmaceutically acceptable carrier.

BACKGROUND OF THE INVENTION

Carcinoma of the prostate is among the most common forms of cancer and of cancer mortality in males. External beam radiation therapy (hereinafter, radiotherapy) is widely used for patients with clinically localized carcinoma of the prostate and is standard therapy for patients diagnosed with extensive local disease (American Joint Committee on Cancer). Radiotherapy also is used for patients with clinically localized carcinoma of the bladder, rectum, uterus and cervix.

Acute effects of radiotherapy on normal tissue are observed during and immediately following a course of radiotherapy. The major complication of radiotherapy, which impinges on the bladder area, is its effect on urinary bladder function resulting in radiation cystitis. Radiation cystitis is defined in terms of bladder pain, increased urinary urgency, increased voiding frequency and increased nocturia. Its duration is usually 3 to 6 months, but can be 24 months or longer. Moreover, serious delayed urinary complications involving lifestyle altering symptoms or requiring hospitalization are observed in 2–7% of patients undergoing radiotherapy for prostate cancer.

It is hypothesized that radiation of the bladder area induces disruption of the glycosaminoglycan (GAG) layer, which lines the inner surface of the urinary bladder. This GAG layer consists of mucopolysaccharides attached to a core protein that, in turn, is bound to a central hyaluronic acid string. This highly viscous, highly hydrophilic GAG layer protects the bladder epithelium against irritants in the urine including, but not limited to, microorganisms, pathogens, microcrystals, proteins, calcium, urea and carcinogens (Nickel et al. 1993. Journal of Urology, 149:716). When this protective barrier is damaged, the bladder epithelium becomes permeable to urinary irritants, resulting in symptoms of bladder pain, increased urinary urgency, increased voiding frequency and increased nocturia. Other symptoms can include, but are not limited to, dysuria, heamaturia, arthritis, spastic colon, low grade fever and irritability.

Methods for treating existing interstitial cystitis include, but are not limited to, hydraulic distention of the urinary bladder, oral amitriptyline or sodium pentosanpolysulfate, intravesical instillation of dimethyl-sulfoxide, oxychlorosene sodium, silver nitrate, heparin, angiostatic steroids, pentosanpolysulfate and hyaluronic acid.

However, what is needed is a method for protecting the urinary bladder from the effects of the radiotherapy so as to prevent, reduce and treat the radiation cystitis caused by radiotherapy that impinges on the bladder area.

SUMMARY OF THE INVENTION

A method is provided for preventing, reducing and treating radiation cystitis caused by radiotherapy that impinges on the urinary bladder of an animal, including a human, comprising administering into the bladder of the animal a composition comprising HA, having an average molecular weight of not less than $2 \times 10^5$ Daltons, and a pharmaceutically acceptable carrier, wherein the HA is administered in an amount effective to prevent, reduce and treat the radiation cystitis.

It is an object of the present invention to provide a method for preventing radiation cystitis.

It is another object of the present invention to provide a method for preventing radiation cystitis that has minimal side effects.

It is another object of the present invention to provide a method for preventing radiation cystitis that is minimally invasive.

It is another object of the present invention to provide a method for preventing radiation cystitis in an individual undergoing radiotherapy for bladder cancer.

It is another object of the present invention to provide a method for preventing radiation cystitis in an individual undergoing radiotherapy for prostate cancer.

It is another object of the present invention to provide a method for preventing radiation cystitis in an individual undergoing radiotherapy for rectal cancer.

It is another object of the present invention to provide a method for preventing radiation cystitis in an individual undergoing radiotherapy for uterine cancer.

It is another object of the present invention to provide a method for preventing radiation cvstitis in an individual undergoing radiotherapy for cervical cancer.

It is another object of the present invention to provide a method for reducing radiation cystitis It is another object of the present invention to provide a method for reducing radiation cystitis that has minimal side effects.

It is another object of the present invention to provide a method for reducing radiation cystitis that is minimally invasive.

It is another object of the present invention to provide a method for reducing radiation cystitis in an individual undergoing radiotherapy for bladder cancer.

It is another object of the present invention to provide a method for reducing radiation cystitis in an individual undergoing radiotherapy for prostate cancer.

It is another object of the present invention to provide a method for reducing radiation cystitis in an individual undergoing radiotherapy for rectal cancer.

It is another object of the present invention to provide a method for reducing radiation cystitis in an individual undergoing radiotherapy for uterine cancer.

It is another object of the present invention to provide a method for reducing radiation cystitis in an individual undergoing radiotherapy for cervical cancer.

It is another object of the present invention to provide a method for treating radiation cystitis after completion of a course of radiotherapy.

It is another object of the present invention to provide a method for treating radiation cystitis after completion of a course of radiotherapy that has minimal side effects.

It is another object of the present invention to provide a method for treating radiation cystitis after completion of a course of radiotherapy that is minimally invasive.

It is another object of the present invention to provide a method for treating radiation cystitis in an individual after completion of a course of radiotherapy for bladder cancer.

It is another object of the present invention to provide a method for treating radiation cystitis in an individual after completion of a course of radiotherapy for prostate cancer.

It is another object of the present invention to provide a method for treating radiation cystitis in individuals after completion of a course of radiotherapy for rectal cancer.

It is another object of the present invention to provide a method for treating radiation cystitis in an individual after completion of a course of radiotherapy for uterine cancer.

It is another object of the present invention to provide a method for treating radiation cystitis in an individual after completion of a course of radiotherapy for cervical cancer.

Other objects, features and advantages of the present invention will become apparent upon reading the following detailed description of the invention when taken in conjunction with the appended claims.

DETAILED DESCRIPTION OF THE INVENTION

As used herein, the word "bladder" refers to the internal surface of the urinary bladder and its associated structures in an animal, including a human.

As used herein, the phrase "associated structures" refers to the renal pelvis, ureters and urethra in an animal, including a human.

As used herein, the phrase "internal surface of the urinary bladder" refers to the transitional epithelium, which lines the urinary bladder and associated structures in an animal, including a human.

As used herein, the phrase "radiation cystitis" refers to symptoms selected from the group consisting of bladder pain, increased urinary urgency, increased voiding frequency and increased nocturia that are associated with radiotherapy that impinges on the bladder.

HA is highly viscous, highly electronegative and highly hydrophilic. It has been found that contacting the bladder with a solution containing an effective concentration of HA and salts thereof, having an average molecular weight of not less than $2 \times 10^5$ Daltons, prior to radiotherapy, during a course of radiotherapy treatments, unexpectedly prevents or reduces the symptoms of radiation cystitis usually caused by radiotherapy for diseases such as, but not limited to, prostate cancer, bladder cancer, rectal cancer, uterine cancer and cervical cancer. It also has been found that contacting the bladder with a solution containing an effective concentration of HA and salts thereof, having an average molecular weight of not less than $2 \times 10^5$ Daltons, subsequent to completion of a course of radiotherapy treatments unexpectedly treats the symptoms of radiation cystitis caused by radiotherapy for diseases such as, but not limited to, prostate cancer, bladder cancer, rectal cancer, uterine cancer and cervical cancer. Preferably the HA has a molecular weight range of about $2 \times 10^5$ to about $3.1 \times 10^6$ Daltons, more preferably of about $2 \times 10^5$ to about $1.9 \times 10^6$ Daltons and most preferably of about $2.5 \times 10^5$ to about $1.2 \times 10^6$ Daltons.

Various methods for the isolation, purification and fractionation of hyaluronic acid are available. These include fractionation of HA derived from cartilage, fractionation of hyaltironic acid derived from bacteria including, but not limited to, streptococcal species, and the purchase of molecular weight fractions of hyaluronic acid from commercial sources including, but not limited to, Fluka Chemical Corporation, Ronkonkoma, N.Y., Genzyme Corporation, Cambridge, Mass. and Lifecore Biomedical, Inc., Chaska, Minn.

For use in the present invention, the HA is solubilized in a pharmaceutically acceptable carrier including, but not limited to, physiological saline and phosphate buffered saline. However, it is to be understood that any of the pharmaceutical carriers known to those skilled in the art to be acceptable for administration into the bladder of an animal can be used in the present invention.

HA is administered into the bladder in an amount between about 5 mg and about 1000 mg, more preferably between about 10 mg and about 500 mg and most preferably between about 25 mg and about 100 mg. The concentration of HA administered into the bladder is preferably from about 0.01 mg/ml to about 100 mg/ml, more preferably from about 0.1 mg/ml to about 50 mg/ml and most preferably from about 0.4 mg/ml to about 25 mg/ml. The volume of HA solution administered into the bladder is between about 1 ml and about 500 ml, more preferably between about 10 ml and about 250 ml and most preferably between about 20 ml and about 100 ml.

To prevent or to reduce radiation cystitis, HA solution can be administered into the bladder prior to a radiotherapy treatment and/or subsequent to a radiotherapy treatment. It can be used in conjunction with each radiotherapy treatment or in conjunction with any multiple of radiotherapy treatments. To treat radiation cystitis, HA solution can be administered into the bladder one or more times after completion of a course of radiotherapy treatments.

Prior to installation of HA solution, residual urine is removed from the bladder using a sterile urethral catheter. The HA solution is then administered into the bladder using, but not limited to, a sterile urethral catheter. However, it is to be understood that any method known to those skilled in the art for administering a pharmaceutical composition into the bladder of an animal can be used in the present invention.

HA solution is administered into the bladder from about 1 minute to about 4 hours prior to a radiotherapy treatment or subsequent to a radiotherapy treatment, more preferably from about 2 minutes to about 2 hours and most preferably from about 5 minutes to about 1 hour. HA solution also is administered into the bladder after completion of a course of radiotherapy treatments. Whether administered prior to a radiotherapy treatment, subsequent to a radiotherapy treatment or after completion of a course of radiotherapy treatments, the HA solution remains in contact with the bladder for a total time of about 1 minute to about 4 hours, more preferably from about 2 minutes to about 2 hours and most preferably from about 5 minutes to about 1 hour.

The HA solution may further include agents such as, but not limited to, antiseptic, antibacterial, antifungal, immunotherapeutic, immunosuppressive, chemotherapeutic, pH modifying, and glycosaminoglycan (in addition to HA) agents. The agent and the amount of the agent to be included in the HA solution are well within the determination of those skilled in the art.

Antibacterial agents include, but are not limited to, aminoglycoside, cephalosporin, gentamycin, macrolide, nitrofurantoin, penicillin, quinolone, sulphonamide, tetracycline, trimethoprim, bacitracin, neomycin, chlorhexidine and mandelamine. Antifungal (antiyeast) agents include, but are not limited to, amphotericin B and fluconazole. Immunotherapeutic agents include, but are not limited to, bacterial cell extracts, mycobacterial cell wall extracts, live and inactivated bacillus Calmette-Guerin (BCG), BCG extracts, cytokines, interferons, interleukins, prostaglandins, and immune stimulants of viral, chemical and molecular biological origin effective for treating disorders of the bladder and the associated cystitis. Immunosuppressive agents include, but not limited to, prostaglandins ($PGE_2$) and corticosteroids. Chemotherapeutic agents include, but are not limited to, cisplatin, cyclophosphamide, doxorubicin (adriamycin), vincristine, mitomicin-C and thiotepa. pH modifying agents include, but are not limited to, sodium acid phosphate and sodium bicarbonate. Glvcosaminoglycans (in addition to HA) include, but are not limited to, heparin, heparan sulfates, pentosanpolysulfate, dermatan sulfates, chondroitin sulfates and keratanosulfates.

EXAMPLE 1

Patient Selection

Inclusion criteria include patients >18 years of age with histologically documented stage T2 or T3 (T3$a$ or T3$b$) prostate carcinoma and PSA within normal range following anti-androgen therapy (<60 years, upper limit of 4.0 ng/ml; 60–69 years, upper limit 4.5 ng/ml; >70 years, upper limit of 6.5 ng/ml). These patients have an ECOG performance status for cancer clinical trials of 0, 1 or 2 (Oken et al. American Journal of Clinical Oncology (CCT), 5:649, 1982), a five-year life expectancy and are available for at least one year. They have normal white blood cell count, platelets, international normalized ratio of prothrombin time and partial thromboplastin time.

Exclusion criteria include patients being treated with investigational drugs, anticholinergics, urinary antiseptics, antihistamines, potent analgesics, corticosteroids, anti-inflammatory agents or any medication or active treatment for interstitial cystitis within 14 days of radiotherapy, patients with clinical evidence of metastatic disease, multiple transurethral resections of bladder tumors or recurring bladder infections or stones, collagen, vascular, or autoimmune disease, ulcerative colitis or regional enteritis, multiple prior abdominal surgical procedures, renal insufficiency (Blood Urea Nitrogen >15 mmol/L, serum creatinine >250 $\mu$mmol/L), hepatic insufficiency (Alanine Aminotransferase and Aspartate Aminotransferase >50% above upper limit of normal), uncontrolled congestive heart failure or uncontrolled ischemic heart disease and previous chemotherapy and/or radiation therapy.

EXAMPLE 2

Pre-therapy (Baseline) Assessment

Pre-therapy pain scale, urinary urgency (urgency) scale, voiding frequency and nocturia are obtained 3 times during week 0 (pre-therapy) using patient recorded (diary) assessments. Pre-therapy symptom index and problem index is assessed 1 time during week 0 using patient administered questionnaires. The scales and indices used are known to those skilled in the art.

Pain scales include the Visual Analog Scale (VAS 0–10 cm), the 6 Point Behavioral Rating Scale (BRS-6) and 5 Point Verbal Rating Scale (VRS-5). Urgency is defined as a strong need to urinate with little or no warning. Urgency scales include the Visual Analog Scale (VAS 0–10 cm) and the Point Verbal Rating Scale (VRS-5). Voiding frequency measures the frequency of urination during a 24 hour time period and nocturia measures the frequency of waking up to urinate during sleep. The symptom index measures radiation cystitis symptoms, which occur during a specified time period (O'Leary et al., Journal of Urology 155(515):439A, 1996). The problem index measures lifestyle problems related to radiation cystitis.

EXAMPLE 3

Radiation Protocol

A radiotherapy dose of 18–220 cGY per day is given 5 days per week for 6 weeks and 3 times per week for 1 additional week (33 treatments) resulting in a total dose of 6600 cGY.

EXAMPLE 4

HA Protocol

HA solution is administered into the bladder about 30 minutes prior to radiotherapy 3 times per week (alternate days) for 6 weeks and 2 times per week for 1 additional week (20 treatments).

To do this, a urethral catheter is introduced into the bladder under aseptic conditions, residual urine is removed and the volume recorded. Fifty ml of sterile PBS containing about 40 mg of HA, having an average molecular weight of about $6.5 \times 10^5$ Daltons (range $5 \times 10^5$ to $7.3 \times 10^5$ Daltons), is administered into the bladder through the catheter. The HA solution is maintained in the bladder for about 30 minutes, the HA solution is voided and the radiotherapy is begun.

EXAMPLE 5

During Therapy Assessment

During the 7 weeks of radiotherapy, pain scale, urgency scale, voiding frequency and nocturia are obtained 3 times per week using patient recorded (diary) assessments as in Example 2. Symptom index and problem index is assessed at weeks 4 and 8 using patient administered questionnaires as in Example 2.

EXAMPLE 6

Outcome Criteria

As pain scale, urgency scale, symptom index and problem index are subjective assessments, each patient undergoing radiotherapy for prostate cancer was used as his own control. To do this, the average of pain scales, urgency scales, voiding frequencies and nocturia reported during weeks 6 and 7 of radiotherapy and symptom index and problem index reported at week 8 (post-therapy) were compared to the average of pain scales, urgency scales, voiding frequencies and nocturia and symptom index and problem index reported during week 0 (pre-therapy).

Outcome criteria include:

A. HA Administered During Course of Radiotherapy:

1. Prevention of symptoms of radiation cystitis—decreases or no increases in average pain scale, average urgency scale, average voiding frequency or average nocturia during weeks 6 and 7 of radiotherapy compared to week 0 and decreases or no increases in symptom index and in problem index at week 8 compared to week 0.

2. Reduction in symptoms of radiation cystitis—minimal increases in average pain scale of $\leq 1.0$, average urgency scale of ≦1.0, average voiding frequency of ≦5, and average nocturia of ≦3 during weeks 6 and 7 of radiotherapy compared to week 0 and minimal increases in symptom index of ≦3 and problem index of ≦3 at week 8 compared to week 0.

3. Ineffective to prevent or reduce symptoms of radiation cystitis—significant increases in average pain scale of >1.0, average urgency scale of >1.0, average voiding frequency of >5, and average nocturia of >3 during weeks 6 and 7 of radiotherapy compared to week 0 and significant increases in symptom index of >3 and problem index of >3 at week 8 compared to week 0.

4. Patient withdraws or is withdrawn from the study.

B. HA Administered at Completion of a Course of Radiotherapy:

1. Treatment of symptoms of radiation cystitis—significant decreases in average pain scale of ≧1.0, average urgency scale of ≧1.0, average voiding frequency of ≧5, and average nocturia of ≧3 during weeks 12 and 13 after radiotherapy compared to weeks 6 and 7 of radiotherapy and decreases in symptom index of ≧3 and problem index of ≧3 at week 14 after radiotherapy compared to weeks 6 and 7 of radiotherapy.

2. Ineffective to treat symptoms of radiation cystitis—minimal decreases in average pain scale of <1.0, average urgency scale of <1.0, average voiding frequency of <5, and average nocturia of <3 during weeks 12 and 13 after radiotherapy compared to weeks 6 and 7 of radiotherapy and decreases in symptom index of <3 and problem index of <3 at week 14 after radiotherapy compared to weeks 6 and 7 of radiotherapy.

3. Patient withdraws or is withdrawn from the study.

EXAMPLE 7

Radiotherapy without HA

Patients, selected as in Example 1, receive radiotherapy as in Example 3. These patients have increases in average pain scale >1.0, average urgency scale of >1.0, average voiding frequency of >5 and average nocturia of >3 during weeks 6 and 7 of radiotherapy compared to week 0 and increases in symptom index of >3 and in problem index of >3 at week 8 compared to week 0.

By weeks 6 and 7, each of these patients reports passage of small amounts of urine with burning pain, voiding frequencies of >20 times per day and nocturia of >8 times per night.

Therefore, patients who do not receive administration of HA into the bladder, prior to radiotherapy treatments during a course of radiotherapy that impinges on the bladder, develop the bladder pain, increased urgency, increased voiding frequency and increased nocturia symptomatic of radiation cystitis.

EXAMPLE 8

Radiotherapy with Concurrent HA

Five patients, selected as in Example 1, elected to receive HA as in Example 4 prior to radiotherapy treatments during the course of their radiotherapy for prostate cancer as in Example 3.

Table 1 shows results obtained for Patient A during weeks 1–7 of radiotherapy and at the completion of radiotherapy (week 8).

TABLE 1

Patient A

| Week | Day | Pain VAS | Urgency VAS | Frequency Times/24 h | Nocturia Times | Symptom Index | Problem Index |
|---|---|---|---|---|---|---|---|
| 0 | 3 | ND | ND | ND | ND | 3 | 0 |
| 1 | 1 | 0 | 0.1 | 8 | 0 | | |
| | 2 | ND | 0.1 | 8 | 0 | | |
| | 3 | ND | ND | 8 | 0 | | |
| 2 | 1 | 0.1 | ND | 5 | 0 | | |
| | 2 | ND | ND | 7 | 0 | | |
| | 3 | ND | ND | 7 | 0 | | |
| 3 | 1 | 0.1 | 0.2 | 8 | 0 | | |
| | 3 | ND | 1.0 | 7 | 1 | | |
| 4 | 1 | ND | 0.0 | 7 | 1 | 2 | 1 |
| | 2 | ND | ND | 7 | 1 | | |
| | 3 | 0.1 | 0.1 | 7 | 1 | | |
| 5 | 1 | ND | ND | 8 | 0 | | |
| | 2 | 0.2 | 0.2 | 7 | 1 | | |
| | 3 | 0.2 | 0.4 | 7 | 3 | | |
| 6 | 1 | ND | ND | 7 | 1 | | |
| | 2 | 0.2 | 0.1 | 7 | 1 | | |
| | 3 | 0.2 | 0.2 | 8 | 2 | | |
| 7 | 1 | 0.2 | 0.2 | 7 | 2 | | |
| | 2 | 0.2 | ND | 7 | 2 | | |
| 8 | 1 | | | | | 2 | 1 |

As pre-therapy (week 0) data for pain scale, urgency scale, voiding frequency and nocturia were not available for this patient, week 1 averages were used as baseline. For week 1, pain scale was 0.0 and increased to 0.2 during weeks 6 and 7 of radiotherapy. For week 1, urgency scale was 0.0 and increased to 0.17 during weeks 6 and 7 of radiotherapy. For week 1, voiding frequency was 8.0 and decreased to 7.3 during weeks 6 and 7 of radiotherapy. For week 1, nocturia was 0.0 and increased to 1.7 during weeks 6 and 7 of radiotherapy. The symptom index decreased from 3 to 2 and the problem index increased from 0 to 1 between weeks 0 and 8.

These data show that administration of HA into the bladder of Patient A prior to radiotherapy treatments during a course of radiotherapy either prevented or reduced the pain, increased urgency, increased voiding frequency and increased nocturia usually associated with radiotherapy for the treatment of prostate cancer.

Table 2 shows results obtained for Patient B prior to radiotherapy (week 0), during radiotherapy (weeks 1–7) and at the completion of radiotherapy (week 8).

TABLE 2

Patient B

| Week | Day | Pain VAS | Urgency VAS | Frequency Times/24 h | Nocturia Times | Symptoms Index | Problems Index |
|---|---|---|---|---|---|---|---|
| 0 | 1 | 0.2 | 0.3 | 5 | 3 | 5 | 8 |
| | 2 | 0.1 | 0.3 | 11 | 3 | | |
| | 3 | 0.1 | 0.1 | 9 | 2 | | |
| 1 | 1 | 0.1 | 0.2 | 8 | 3 | | |
| | 2 | 0.2 | 0.2 | 11 | 3 | | |
| | 3 | 0.1 | 0.2 | 10 | 4 | | |
| 2 | 1 | 0.2 | 0.8 | 8 | 5 | | |
| | 2 | 0.2 | 0.8 | 11 | 6 | | |
| | 3 | 0.1 | 0.7 | 12 | 4 | | |
| 3 | 1 | 0.1 | 0.8 | 12 | 3 | | |
| | 2 | 0.1 | 0.6 | 15 | 4 | | |
| | 3 | 0.1 | 0.6 | 13 | 3 | | |

TABLE 2-continued

Patient B

| Week | Day | Pain VAS | Urgency VAS | Frequency Times/24 h | Nocturia Times | Symptoms Index | Problems Index |
|---|---|---|---|---|---|---|---|
| 4 | 1 | 0.1 | 0.9 | 12 | 4 | 4 | 9 |
|   | 2 | 0.1 | 0.5 | 14 | 4 |   |   |
|   | 3 | 0.1 | 0.1 | 11 | 4 |   |   |
| 5 | 1 | 0.1 | 0.8 | 10 | 4 |   |   |
|   | 2 | 0.0 | 0.0 | 11 | 4 |   |   |
|   | 3 | 0.1 | 1.0 | 13 | 4 |   |   |
| 6 | 1 | 0.1 | 0.5 | 13 | 2 |   |   |
|   | 2 | 0.1 | 0.5 | 12 | 2 |   |   |
|   | 3 | 0.1 | 0.5 | 14 | 3 |   |   |
| 7 | 1 | 0.1 | 1.0 | 15 | 4 |   |   |
|   | 2 | 0.1 | 0.5 | 13 | 5 |   |   |
| 8 | 1 |   |   |   |   | 4 | 7 |

For week 0, pain scale was 0.13 and remained relatively unchanged at 0.10 during weeks 6 and 7 of radiotherapy. For week 0, urgency scale was 0.23 and increased to 0.60 during weeks 6 and 7 of radiotherapy. For week 0, voiding frequency was 8.3 and increased to 13.4 during weeks 6 and 7 of radiotherapy. For week 0, nocturia was 2.7 and increased to 3.2 during weeks 6 and 7 of radiotherapy. The symptom index decreased from 5 to 4 and the problem index decreased from 8 to 7 between weeks 0 and 8.

These data show that administration of HA into the bladder of Patient B prior to radiotherapy treatments during a course of radiotherapy reduced the pain, increased urgency, increased voiding frequency and increased nocturia usually associated with radiotherapy for the treatment of prostate cancer.

Table 3 shows results obtained for Patient C prior to radiotherapy (week 0), during radiotherapy (weeks 1–7) and at the completion of radiotherapy (week 8).

TABLE 3

Patient C

| Week | Day | Pain VAS | Urgency VAS | Frequency Times/24 h | Nocturia Times | Symptoms Index | Problems Index |
|---|---|---|---|---|---|---|---|
| 0 | 1 | 0.2 | 6.8 | 7 | 2 | 6 | 4 |
|   | 2 | 0.2 | 5.0 | 7 | 1 |   |   |
|   | 3 | 0.2 | 4.8 | 7 | 2 |   |   |
| 1 | 1 | 0.2 | 5.0 | 5 | 1 |   |   |
|   | 2 | 0.2 | 5.1 | 8 | 2 |   |   |
|   | 3 | 0.2 | 5.0 | 9 | 1 |   |   |
| 2 | 1 | 0.2 | 4.9 | 10 | 1 |   |   |
|   | 2 | 0.1 | 5.2 | 11 | 2 |   |   |
|   | 3 | 0.2 | 2.6 | 6 | 3 |   |   |
| 3 | 1 | 0.1 | 5.2 | 6 | 2 |   |   |
|   | 2 | 0.2 | 5.2 | 8 | 2 |   |   |
|   | 3 | 0.2 | 2.5 | 7 | 3 |   |   |
| 4 | 1 | 0.1 | 4.3 | 8 | 4 | 7 | 8 |
|   | 2 | 0.1 | 4.3 | 11 | 3 |   |   |
|   | 3 | 0.1 | 2.0 | 8 | 1 |   |   |
| 5 | 1 | 0.1 | 4.3 | 12 | 2 |   |   |
|   | 2 | 0.0 | 2.0 | 9 | 2 |   |   |
|   | 3 | 0.1 | 4.3 | 10 | 3 |   |   |
| 6 | 1 | 0.1 | 2.0 | 10 | 4 |   |   |
|   | 2 | 0.1 | 2.0 | 12 | 2 |   |   |
|   | 3 | 0.1 | 2.0 | 9 | 2 |   |   |
| 7 | 1 | 0.1 | 2.0 | 11 | 1 |   |   |
|   | 2 | 0.1 | 2.0 | 10 | 4 |   |   |
| 8 | 1 |   |   |   |   | 11 | 12 |

For week 0, pain scale was 0.20 and remained relatively unchanged at 0.10 during weeks 6 and 7 of radiotherapy. For week 0, urgency scale was 5.5 and decreased to 2.0 during weeks 6 and 7 of radiotherapy. For week 0, frequency was 7 and increased to 10.4 during weeks 6 and 7 of radiotherapy. For week 0, nocturia was 1.7 and increased to 2.6 during weeks 6 and 7 of radiotherapy. The symptom index increased from 8 to 11 and the problem index increased from 5 to 12 between weeks 0 and 8.

Although Patient C reported no change in pain scale, a decrease in urgency scale and minimal increases in voiding frequency and nocturia between week 0 and weeks 6 and 7, he reported significant increases in symptom index and in problem index between weeks 0 and 8. Nevertheless, these data show that administration of HA into the bladder of Patient C prior to radiotherapy treatments during a course of radiotherapy either prevented or reduced the pain, increased urgency, increased voiding frequency and increased nocturia usually associated with radiotherapy for the treatment of prostate cancer.

Table 4 shows results obtained for Patient D prior to radiotherapy (week 0), during radiotherapy (weeks 1–7) and at the completion of radiotherapy (week 8).

TABLE 4

Patient D

| Week | Day | Pain VAS | Urgency VAS | Frequency Times/24 h | Nocturia Times | Symptoms Index | Problems Index |
|---|---|---|---|---|---|---|---|
| 0 | 1 | 0.0 | 4.5 | 9 | 3 | 3 | 1 |
|   | 2 | 0.0 | 3.5 | 9 | 3 |   |   |
|   | 3 | 0.0 | 2.2 | 8 | 3 |   |   |
| 1 | 1 | 0.0 | 3.2 | 10 | 5 |   |   |
|   | 2 | 0.0 | 1.9 | 8 | 2 |   |   |
|   | 3 | 0.0 | 1.8 | 7 | 2 |   |   |
| 2 | 1 | 0.0 | 1.8 | 10 | 3 |   |   |
|   | 2 | 0.0 | 1.9 | 9 | 3 |   |   |
|   | 3 | 0.0 | 1.6 | 11 | 3 |   |   |
| 3 | 1 | 0.0 | 2.2 | 11 | 5 |   |   |
|   | 2 | 0.0 | 4.5 | 10 | 3 |   |   |
|   | 3 | 0.0 | 3.1 | 10 | 4 |   |   |
| 4 | 1 | 0.0 | 2.8 | 11 | 5 | 4 | 1 |
|   | 2 | 0.0 | 6.8 | 9 | 3 |   |   |
|   | 3 | 0.0 | 1.7 | 11 | 4 |   |   |
| 5 | 1 | 0.0 | 2.3 | 11 | 4 |   |   |
|   | 2 | 0.0 | 3.9 | 10 | 3 |   |   |
|   | 3 | 0.0 | 3.0 | 10 | 4 |   |   |
| 6 | 1 | 0.0 | 3.4 | 12 | 6 |   |   |
|   | 2 | 0.0 | 4.2 | 12 | 5 |   |   |
|   | 3 | 0.0 | 3.0 | 12 | 4 |   |   |
| 7 | 1 | 0.0 | 2.5 | 13 | 4 |   |   |
| 8 | 1 |   |   |   |   | 4 | 1 |

For week 0, pain scale was 0.0 and remained unchanged at 0.0 during weeks 6 and 7 of radiotherapy. For week 0, urgency scale was 3.4 and remained essentially unchanged at 3.3 during weeks 6 and 7 of radiotherapy. For week 0, frequency was 8.7 and increased to 12.2 during weeks 6 and 7 of radiotherapy. For week 0, nocturia was 3.0 and increased to 4.7 during weeks 6 and 7 of radiotherapy. The symptom index increased from 3 to 4 and the problem index remained unchanged at 1 between weeks 0 and 8.

These data show that administration of HA into the bladder of Patient D prior to radiotherapy during a course of radiotherapy treatments either prevented or reduced the pain, increased urgency, increased voiding frequency and increased nocturia usually associated with radiotherapy for the treatment of prostate cancer.

A fifth patient, Patient E, was withdrawn from the study after two weeks of HA treatment due to a pre-therapy urinary tract bacterial infection which did not improve with antibiotic treatment.

In summary, Patients A, B and D treated with HA as in Example 4, prior to radiotherapy treatments, showed either decreases, no increases or minimal increases in average pain scale, average urgency scale, average voiding frequency, average nocturia, pain index and symptom index after 33 radiotherapy treatments during a 7 week period. Patient D, showed no increase in average pain scale, a decrease in average urgency scale, minimal increases in average voiding frequency, average nocturia and problem index and a significant increase in symptom index.

Therefore, patients administered HA into the bladder prior to radiotherapy treatments, during a course of radiotherapy that impinges on the bladder, did not develop the bladder pain, increased urinary urgency, increased voiding frequency and increased nocturia symptomatic of radiation cystitis.

EXAMPLE 9

Radiotherapy Followed by HA

Patients, selected as in Example 1, receive radiotherapy for 7 weeks as in Example 3. At week 8, each of these patients shows significant symptoms of radiation cystitis. At this time, each patient is treated with HA as in Example 4 except that the HA is administered 3 times per week (alternate days) for 6 weeks (weeks 8–13) for a total of 18 treatments or until the radiation cystitis symptoms resolve. Pre-therapy assessments, as in Example 2, are done during weeks 6 and 7 of radiotherapy. Therapy assessments, as in Example 5, are done during weeks 8–13 or until symptoms resolve. Final symptom index and problem index are done at week 14 or when radiation cystitis symptoms resolve.

Each of the patients receiving HA for treatment of radiation cystitis, following a complete course of radiotherapy for prostate cancer, show a decrease in bladder pain, urinary urgency, voiding frequency and nocturia after from 1 to 6 weeks of HA treatment (weeks 8–13), and a decrease in problem index and symptom index by week 14.

Therefore, administration of HA into the bladder of patients having radiation cystitis, following a course of radiotherapy treatments for prostate cancer, decreases the pain, urinary urgency, voiding frequency and nocturia symptomatic of radiation cystitis.

It should be understood, of course, that the foregoing relates only to a preferred embodiment of the present invention and that numerous modifications or alterations may be made therein without departing from the spirit and the scope of the invention as set forth in the appended claims.

I claim:

1. A method of preventing radiation-induced cystitis of the bladder area comprising instilling into the bladder of a human or an animal, a composition comprising hyaluronic acid having an average molecular weight of not less than about $2 \times 10^5$ Daltons, and a pharmaceutically acceptable carrier, followed by administering radiotherapy treatment to the bladder area.

2. The method of claim 1, wherein the average molecular weight of the hyaluronic acid is between about $2 \times 10^5$ and about $3.1 \times 10^6$ Daltons.

3. The method of claim 1, wherein the hyaluronic acid is an amount between about 5 mg and about 1000 mg.

4. The method of claim 1, wherein the composition is administered in a volume of between about 1 ml and about 500 ml of the composition.

5. The method of claim 1, wherein the administration of the composition occurs about 1 minute to about 4 hours prior to the radiotherapy treatment.

6. The method of claim 1, wherein the administration of the composition is such that the composition remains in the bladder for about 1 minute to about 4 hours prior to the radiotherapy treatment.

7. The method of claim 1, wherein the radiotherapy of the bladder area is for treatment of a cancer, wherein the cancer is bladder cancer, prostate cancer, rectal cancer, uterine cancer or cervical cancer.

8. The method of claim 1, wherein the radiotherapy of the bladder area is for treatment of prostate cancer.

9. The method of claim 1, wherein the byaluronic acid is an amount between about 10 mg and about 500 mg.

10. The method of claim 1, wherein the hyaluronic acid is an amount between about 25 mg and about 100 mg.

11. The method of claim 1, wherein the composition is administered in a volume of between about 10 ml and about 250 ml.

12. The method of claim 1, wherein the composition is administered in a volume of between about 20 ml and about 100 ml.

13. The method of claim 1, wherein the administration of the composition occurs about 2 minutes to about 2 hours prior to the radiotherapy treatment.

14. The method of claim 1, wherein the administration of the composition occurs about 5 minutes to about 1 hour prior to the radiotherapy treatment.

15. A method of reducing radiation-induced cystitis of the bladder area, comprising instilling into the bladder of a human or an animal a composition comprising hyaluronic acid having an average molecular weight of not less than about $2 \times 10^5$ Daltons, and a pharmaceutically acceptable carrier followed by administering radiotherapy treatment to the bladder area.

16. The method of claim 15, wherein the average molecular weight range of the hyaluronic acid is between about $2 \times 10^5$ and about $3.1 \times 10^6$ Daltons.

17. The method of claim 15, wherein the hyaluronic acid is an amount between about 5 mg and about 1000 mg.

18. The method of claim 15, wherein the composition is administered in a volume of between about 1 ml and about 500 ml of the composition.

19. The method of claim 15, wherein the administration of the composition prior to the radiotherapy treatment occurs about 1 minute to about 4 hours prior to the radiotherapy treatment.

20. The method of claim 15, wherein the administration of the composition is such that the composition remains in the bladder from about 1 minute to about 4 hours prior to the radiotherapy treatment.

21. The method of claim 15, wherein the radiotherapy of the bladder area is for treatment of a cancer, wherein the cancer is bladder cancer, prostate cancer, rectal cancer, uterine cancer or cervical cancer.

22. The method of claim 15, wherein the radiotherapy of the bladder area is for treatment of prostate cancer.

23. The method of claim 15, wherein the hyaluronic acid is an amount between about 10 mg and about 500 mg.

24. The method of claim 15, wherein the hyaluronic acid is an amount between about 25 mg and about 100 mg.

25. The method of claim 15, wherein the composition is administered in a volume of between about 10 ml and about 250 ml.

26. The method of claim 15, wherein the composition is administered in a volume of between about 20 ml and about 100 ml.

27. The method of claim 15, wherein the administration of the composition occurs about 2 minutes to about 2 hours prior to the radiotherapy treatment.

28. The method of claim 15, wherein the administration of the composition occurs about 5 minutes to about 1 hour prior to the radiotherapy treatment.

* * * * *